United States Patent
Kim et al.

(10) Patent No.: US 10,434,055 B1
(45) Date of Patent: Oct. 8, 2019

(54) MODELING COMPOSITION CONTAINING COCONUT OIL

(71) Applicants: Ji-Sun Kim, Goyang-si (KR); Baek-Yeon Sung, Goyang-si (KR)

(72) Inventors: Ji-Sun Kim, Goyang-si (KR); Baek-Yeon Sung, Goyang-si (KR)

( * ) Notice: Subject to any disclaimer, the term of this patent is extended or adjusted under 35 U.S.C. 154(b) by 0 days.

(21) Appl. No.: 16/390,888

(22) Filed: Apr. 22, 2019

(30) Foreign Application Priority Data

Sep. 10, 2018 (KR) .................. 10-2018-0107578

(51) Int. Cl.

| | |
|---|---|
| *C08L 3/02* | (2006.01) |
| *C08K 5/01* | (2006.01) |
| *C08K 5/10* | (2006.01) |
| *C08K 5/5353* | (2006.01) |
| *C08L 1/28* | (2006.01) |
| *C08L 91/00* | (2006.01) |
| *G09B 19/10* | (2006.01) |
| *A61K 8/92* | (2006.01) |
| *A61Q 19/00* | (2006.01) |
| *A61K 8/73* | (2006.01) |
| *A61K 8/55* | (2006.01) |
| *A61K 8/31* | (2006.01) |
| *A61K 8/37* | (2006.01) |
| *A61K 8/81* | (2006.01) |

(52) U.S. Cl.
CPC ................ *A61K 8/922* (2013.01); *A61K 8/31* (2013.01); *A61K 8/37* (2013.01); *A61K 8/553* (2013.01); *A61K 8/731* (2013.01); *A61K 8/732* (2013.01); *A61K 8/8129* (2013.01); *A61K 8/8135* (2013.01); *A61K 8/92* (2013.01); *A61Q 19/00* (2013.01); *C08L 3/02* (2013.01); *C08L 2205/03* (2013.01)

(58) Field of Classification Search
CPC . A61K 8/922; A61K 8/31; A61K 8/37; A61K 8/553; A61K 8/731; A61K 8/732; A61K 8/8129; A61K 8/8135; A61K 8/92; A61Q 19/00; C08L 3/02; C08L 2205/03
USPC .......................................................... 524/35
See application file for complete search history.

(56) References Cited

U.S. PATENT DOCUMENTS

| | | | |
|---|---|---|---|
| 2007/0100052 A1* | 5/2007 | Terry Lee ............... | C08L 91/00 524/451 |
| 2013/0274377 A1* | 10/2013 | Doane, Jr. ................ | C08L 3/00 523/219 |

FOREIGN PATENT DOCUMENTS

| | | |
|---|---|---|
| JP | 2004-208612 A | 7/2004 |
| KR | 10-0978692 B1 | 8/2010 |
| KR | 10-1018158 B1 | 2/2011 |
| KR | 20170091335 A * | 8/2017 |

OTHER PUBLICATIONS

KR 10-2017-0091335 A, machine translation, EPO Espacenet. (Year: 2017).*

* cited by examiner

*Primary Examiner* — Josephine L Chang
(74) *Attorney, Agent, or Firm* — Studebaker & Brackett PC

(57) ABSTRACT

Disclosed is a modeling composition containing coconut oil having a moisturizing effect on the skin and exhibiting efficacy on atopic skin, the modeling composition further containing squalane, starch, an emulsifier, and ozokerite, in addition to coconut oil.

6 Claims, 6 Drawing Sheets

MODELING COMPOSITION CONTAINING COCONUT OIL

CROSS REFERENCE TO RELATED APPLICATION

The present application claims priority to Korean Patent Application No. 10-2018-0107578, filed Sep. 10, 2018, the entire content of which is incorporated herein for all purposes by this reference.

BACKGROUND OF THE INVENTION

1. Technical Field

The present invention relates to a modeling composition (clay or oil clay) for model making, and more particularly to a modeling composition causing no skin problems and having a skin-moisturizing effect similar to that of a cosmetic product.

2. Description of the Related Art

The present invention pertains to a modeling composition capable of producing various models, characters, frames, etc., and particularly to a modeling composition capable of being used to make a model, like clay or oil clay.

Clay, which is used for art education for children or is used to make various kinds of models, is generally transformed into a desired shape by the user's hands in order to produce a model, which is then dried for a predetermined period of time and thus hardened, thereby maintaining the shape thereof. As an example of clay, plasticine, which is an inorganic material having high specific gravity, has drawbacks such as poor transportability and formability and is also problematic because water in the plasticine evaporates quickly during the drying process, so that the working time is short and the surface of the resulting model is cracked or easily broken.

With the goal of overcoming the problems of clay, which contains mineral components, the clay disclosed in Korean Patent No. 10-1018158 has been developed, in which clay is artificially manufactured using a natural polymer such as starch or derivatives thereof, and thus becomes lightweight, does not stick to the hands and is easy to transport due to the low weight thereof, and moreover, the surface thereof is soft compared to inorganic clay. However, the clay using a natural polymer is much lighter than the inorganic clay but is still heavy, and during drying, the volume of the clay is reduced so much that the resulting model cracks and tends to severely split and crumble. Furthermore, it is difficult to color the clay, and discoloration may occur during drying.

In order to solve the problems of lightweight clay as above, Korean Patent No. 10-0978692 discloses a lightweight modeling material containing a polyvinylalcohol-based resin, a viscosity modifier, water and a weight-reducing agent, but it is difficult to control the amount of water and the drying speed and thus deformation resistance of the model is deteriorated, which is undesirable. Moreover, conventional modeling compositions are harmful to human bodies and to the environment due to the use of a plasticizer such as phthalate, borate, etc.

Also, the inorganic clay, the starch-containing conventional clay or oil clay, etc. is problematic because the skin of a worker becomes dry upon long modeling work and thus a rash or the like may occur on the skin of a worker having sensitive skin, and hence it is urgently required to develop a modeling composition that does not adversely affect the skin of the worker. In particular, since the modeling composition is mainly used by children for education or as a hobby, the development of an environmentally friendly modeling composition causing no skin problems and thus protecting children having vulnerable skin is more urgent.

CITATION LIST

Patent Literature

Korean Patent No. 10-1018158
Korean Patent No. 10-0978692

SUMMARY OF THE INVENTION

Accordingly, the present invention is intended to provide a modeling composition that causes no skin problems and may exhibit a long-lasting moisturizing effect.

In particular, the present invention is intended to provide a modeling composition having a moisturizing effect by virtue of the use of natural components.

In particular, the present invention is intended to provide a modeling composition composed exclusively of an environmentally friendly material, in lieu of materials harmful to human bodies and the environment, such as phthalate plasticizers, borate, lead and the like.

Although conventional techniques have problems in which, upon storage for a long period of time, mold blooms or offensive odors such as odors caused by bonding agents are generated, the present invention is intended to provide a modeling composition that solves the aforementioned problems.

The present invention provides a modeling composition comprising 5 to 20 wt % of coconut oil, 5 to 10 wt % of carboxymethyl cellulose, 1 to 10 wt % of squalane, 1 to 5 wt % of lecithin, 20 to 30 wt % of ozokerite, and 30 to 60 wt % of starch.

In particular, the modeling composition of the present invention may further comprise 1 to 5 wt % of sorbitan fatty acid ester.

In particular, the modeling composition of the present invention may further comprise 1 to 5 wt % of at least one emulsifier selected from among neutral fatty acid triglyceride, organic acid monoglyceride, glycerin fatty acid ester, polyoxyethylene fatty acid ester, propylene glycol fatty acid ester, an emulsifier for pharmaceuticals, and an emulsifier for cosmetics.

In particular, the modeling composition of the present invention may further comprise 1 to 10 wt % of at least one natural oil selected from among almond oil, *camellia* oil, castor oil, and jojoba oil.

In particular, the modeling composition of the present invention may further comprise 1 to 10 wt % of at least one moisturizer selected from among glycerin, propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol, and mixtures thereof.

In particular, the modeling composition of the present invention may further comprise 5 to 15 wt % of a mixture of water and a mixed resin comprising polyethylene vinyl acetate and polyvinylalcohol.

According to the present invention, a modeling composition contains coconut oil having effects of moisturizing the skin and of preventing and treating atopy so that no skin problems occur on the hands of a worker, and thus, even when a modeling process is performed, the skin of a user does not crack and is not chapped and the moisturizing effect lasts for a long period of time.

Also, according to the present invention, the modeling composition contains an environmentally friendly material, for example, components useful for the skin similar to those of cosmetics, in lieu of materials harmful to human bodies and the environment, such as phthalate plasticizers, borate, lead and the like. Therefore, when the modeling composition of the prevent invention is used by workers, especially children, no problems occur.

Moreover, the modeling composition of the prevent invention can be easily stored because it does not harden for a long time, and remains workable for a long time because it does not harden during work.

DESCRIPTION OF SPECIFIC EMBODIMENTS

Figure 1:
FIGS. 1 to 6 are photographs of models manufactured using the modeling composition of Example 1.
Figure 2:
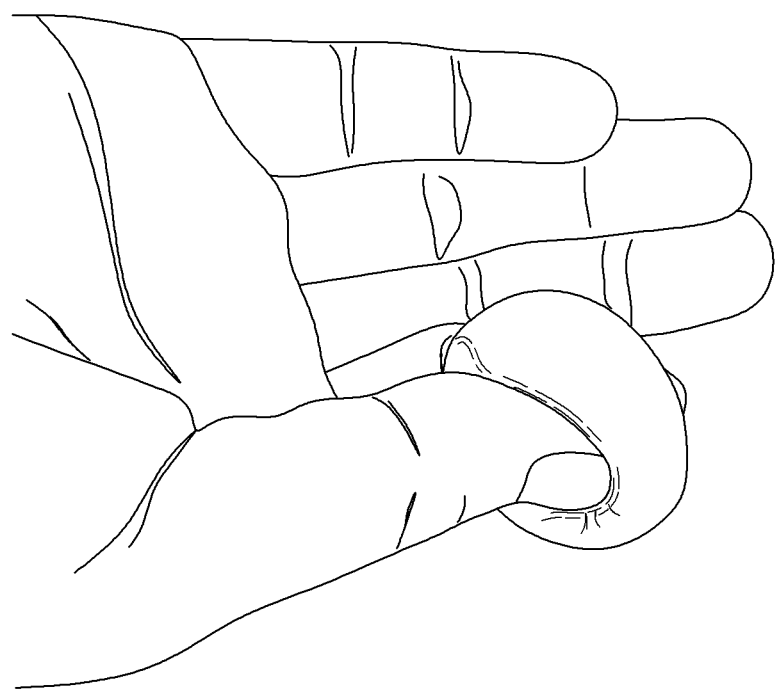
Figure 3:
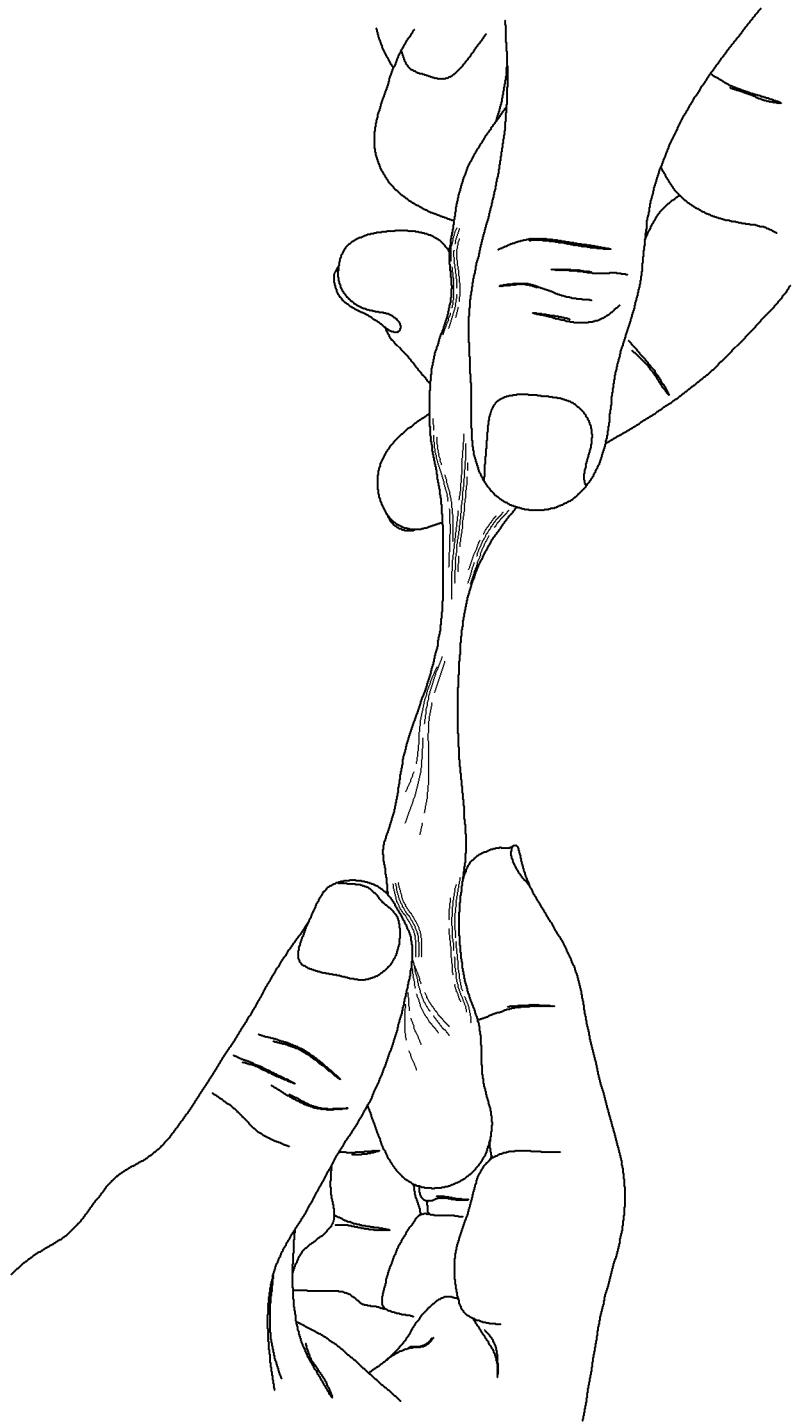
Figure 4:
Figure 5:

The present invention pertains to a modeling composition comprising coconut oil, carboxymethyl cellulose, squalane, lecithin, ozokerite, and starch.

Below is a detailed description of the components thereof.

Coconut Oil

Coconut oil is known to exhibit a variety of beneficial effects on the skin. For example, lauric acid contained in breast milk is an antibacterial, antiviral and antimicrobial substance that boosts the baby's immune system. Since the content of lauric acid contained in coconut oil is at least 10 times that of breast milk, research into coconut oil as a therapeutic agent for atopy is currently ongoing in developed countries including USA, European countries and the like. Furthermore, coconut oil is known to have a strong moisturizing effect and to be effective when applied to dry areas throughout the body.

In order to solve the problem in which the skin of a worker becomes dry and skin problems occur when the conventional modeling composition is used, coconut oil is used in the present invention.

Here, coconut oil is preferably used in an amount of 5 to 20 wt % based on the total weight of the composition of the present invention. If the amount of coconut oil is less than 5 wt %, the effects of the coconut oil may be insufficient. On the other hand, if the amount thereof exceeds 20 wt %, the physical properties of the modeling composition (viscosity, elasticity, hardenability, hardness, etc.) may become unsatisfactory. Hence, it is preferred that the amount of coconut oil fall in the above range, but it may be used in an amount smaller or greater than the above amount if necessary.

Carboxymethyl Cellulose

Carboxymethyl cellulose (CMC), resulting from carboxymethylation of the hydroxyl group of cellulose, may have various qualities depending on the extent of carboxymethylation. Carboxymethyl cellulose may be completely dissolved even in cold water and may be provided in the form of an aqueous solution having high viscosity. Carboxymethyl cellulose is very chemically stable, and in particular, is harmless and nontoxic to the human body and is widely used in various fields as a compound suitable for standards of thickeners, extenders, emulsifying dispersants, adhesives, protective colloid agents and suspension agents, pharmacological standards, and standards for fish-culturing feed additives. In the present invention, carboxymethyl cellulose functions as an emulsifying dispersant.

Here, carboxymethyl cellulose is preferably used in an amount of 5 to 10 wt % based on the total weight of the composition of the present invention. If the amount thereof is less than 5 wt %, the effects as an emulsifier are insignificant. On the other hand, if the amount thereof exceeds 10 wt %, the physical properties of the modeling composition may become unsatisfactory. Hence, it is preferred that the amount of carboxymethyl cellulose fall in the above range, but it may be used in an amount smaller or greater than the above amount if necessary.

Squalane

Squalane is mainly made by adding hydrogen to squalene obtained from deep-sea shark liver oil. Squalane may also be obtained from olive oil, etc., in addition to the shark oil, and when extracted from olive oil, it is called "vegetable squalane". In recent years, the use of vegetable squalane has been increasing, reflecting a general preference for vegetable ingredients. Squalane is a strong and stable material with good ability to withstand ultraviolet rays, heat and air, and has a very low freezing point relative to the molecular weight thereof and excellent permeability. It has less of an oily sensation than other oily materials, has good permeability and feels familiar to the skin and causes little skin irritation. Because of these properties, it is widely used in basic cosmetics. Furthermore, squalane is a component that is contained in human sebum, and has moisturizing, astringent, and softening effects.

In the present invention, squalane is used as one of the active ingredients for preventing skin problems, and the amount thereof is preferably 1 to 10 wt % based on the total weight of the composition of the present invention. If the amount thereof is less than 1 wt %, the squalane content is too small to be effective. On the other hand, if the amount thereof exceeds 10 wt %, the amounts of the other components may be reduced, and the properties of the modeling composition may deteriorate.

Lecithin

Lecithin is a phospholipid, which is a major constituent of biological membranes, such as cell membranes, the endoplasmic reticulum, and mitochondria, and functions as the only natural emulsifier in nature. In the present invention, lecithin also plays a role as an emulsifier in addition to the above-mentioned carboxymethyl cellulose.

The amount thereof may be 1 to 5 wt % based on the total weight of the composition of the present invention. If the amount thereof is less than 1 wt %, the effect of lecithin as an emulsifier is insignificant. On the other hand, if the amount thereof exceeds 5 wt %, the typical properties of a modeling composition may deteriorate. Hence, it is preferred that the amount of lecithin fall in the above range, but it may be used in an amount smaller or greater than the above amount if necessary.

Ozokerite

Ozokerite is a hydrocarbon wax derived from minerals or petroleum materials and is used as a binder, an emulsion stabilizer, or a thickener. It imparts an oily sensation to the skin. In the present invention, ozokerite prevents powdering, which is a disadvantage of the resin component during work, and facilitates mixing with oily and aqueous inks to thus increase the freedom of color expression.

Furthermore, the period of time required to harden the modeling composition may be adjusted depending on the amount of ozokerite that is added, and ozokerite is responsible for preventing clay from sticking to the hands of a worker.

Here, the amount of ozokerite is preferably 20 to 30 wt % based on the total weight of the composition of the present invention. If the amount thereof is less than 20 wt %, the effects of ozokerite are insignificant. On the other hand, if the amount thereof exceeds 30 wt %, the properties of starch as a main component thereof may deteriorate. Hence, it is preferred that the amount of ozokerite fall in the above range, but it may be used in an amount smaller or greater than the above amount if necessary.

In addition, ceresin, microwax, beeswax, or Vaseline may be used in place of ozokerite, or may be used in combination with ozokerite.

Starch

In the present invention, starch is used as a filling material (body) for a model. Starch is not only harmless to the human body, but is also capable of being mixed with aqueous and oily inks, and thus enables free color expression. In the present invention, examples of starch may include various starches such as potato starch, corn starch, sweet potato starch, and wheat starch, which may be used alone or in combination. Starch is preferably used in an amount of 30 to 60 wt % based on the total weight of the composition of the present invention.

Additional Components

As an additional emulsifier, sorbitan fatty acid ester may be used in an amount of 1 to 5 wt % based on the total weight of the composition of the present invention. Also, various emulsifiers may be further added, and the modeling composition of the present invention may further contain 1 to 5 wt % of at least one emulsifier selected from among neutral fatty acid triglyceride, organic acid monoglyceride, glycerin fatty acid ester, polyoxyethylene fatty acid ester, propylene glycol fatty acid ester, an emulsifier for pharmaceuticals, and an emulsifier for cosmetics.

Also, in order to prevent skin problems when the worker touches the composition of the present invention and to impart a skin-moisturizing effect similar to that of a cosmetic product, the modeling composition of the present invention may further contain 1 to 10 wt % of at least one natural oil selected from among almond oil, *camellia* oil, castor oil, and jojoba oil.

Also, a polyhydric alcohol-type cosmetic moisturizer may be used for the modeling composition of the present invention. The moisturizer helps to increase the effectiveness of emollients, reduce keratin, stimulate the removal of formed keratin, and improve a skin tactile sensation. The modeling composition of the present invention may further contain 1 to 10 wt % of a typical polyhydric alcohol selected from among glycerin, alkylene polyol and derivatives thereof, such as propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol, and mixtures thereof.

Also, the modeling composition of the present invention may further contain 5 to 15 wt % of a mixture of water and a mixed resin comprising polyethylene vinyl acetate and polyvinylalcohol. The mixed resin and water may be mixed at a ratio of approximately 1:1, but either one of them may be used in a larger amount as needed. By virtue of the resin component, when the worker touches the composition of the present invention with the hands, the elasticity and viscosity increase further.

EXAMPLES

A better understanding of the present invention will be given through the following examples.

Example 1

A composition of the present invention was prepared by heating and mixing 10 wt % of coconut oil, 7 wt % of carboxymethyl cellulose, 5 wt % of squalane, 3 wt % of lecithin, 20 wt % of ozokerite, and 55 wt % of corn starch using a heater. Based on the results of tactile tests thereon, the composition was easy to touch and did not harden and was soft for a long time. The hands did not crack during or after work, and the skin felt moist and thus the moisturizing effect was confirmed. After hand washing, the user reported a soft and smooth sensation.

Figure 6:
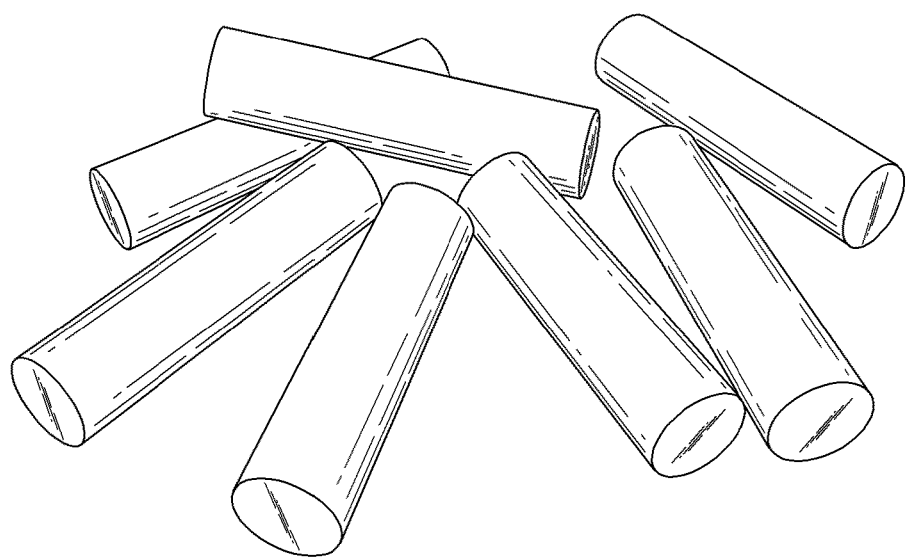

Various shapes shown in FIGS. 1 to 5 were made using the modeling composition of Example 1. In particular, as shown in FIG. 6, the composition of the present invention was able to realize various colors.

Example 2

A composition of the present invention was prepared by heating and mixing 5 wt % of coconut oil, 7 wt % of carboxymethyl cellulose, 5 wt % of squalane, 3 wt % of lecithin, 20 wt % of ozokerite, and 60 wt % of potato starch using a heater. Based on the results of tactile tests thereon, the touch and moisturizing effects were slightly reduced compared to Example 1, but there was still no cracking of the hands during or after work, and the moisturizing effect was exhibited. After hand washing, the user reported a soft and smooth sensation.

Example 3

A composition of the present invention was prepared by heating and mixing 10 wt % of coconut oil, 7 wt % of carboxymethyl cellulose, 5 wt % of squalane, 3 wt % of lecithin, 20 wt % of ozokerite, 3 wt % of sorbitan fatty acid ester and 52 wt % of corn starch using a heater. Based on the results of tactile tests thereon, results similar to Example 1 were exhibited.

Example 4

A composition of the present invention was prepared by heating and mixing 10 wt % of coconut oil, 7 wt % of carboxymethyl cellulose, 5 wt % of squalane, 3 wt % of lecithin, 20 wt % of ozokerite, 3 wt % of sorbitan fatty acid ester, 5 wt % of a mixture of water and a mixed resin comprising polyethylene vinyl acetate and polyvinylalcohol at 1:1 (resin:water=1:1), and 47 wt % of corn starch using a heater. Based on the results of tactile tests thereon, results similar to Example 1 were exhibited, and also, elasticity and viscosity were high compared to Examples 1 to 3 due to the addition of the mixture of water and mixed resin.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A modeling composition, comprising 5 to 20 wt % of coconut oil, 5 to 10 wt % of carboxymethyl cellulose, 1 to 10 wt % of squalane, 1 to 5 wt % of lecithin, 20 to 30 wt % of ozokerite, and 30 to 60 wt % of starch.

2. The modeling composition of claim 1, further comprising 1 to 5 wt % of sorbitan fatty acid ester.

3. The modeling composition of claim 1, further comprising 1 to 5 wt % of at least one emulsifier selected from among neutral fatty acid triglyceride, organic acid monoglyceride, glycerin fatty acid ester, polyoxyethylene fatty acid ester, propylene glycol fatty acid ester, an emulsifier for pharmaceuticals, and an emulsifier for cosmetics.

4. The modeling composition of claim 1, further comprising 1 to 10 wt % of at least one natural oil selected from among almond oil, camellia oil, castor oil, and jojoba oil.

5. The modeling composition of claim 1, further comprising 1 to 10 wt % of at least one moisturizer selected from among glycerin, propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol, and mixtures thereof.

6. The modeling composition of claim 1, further comprising 5 to 15 wt % of a mixture of water and a resin comprising polyethylene vinyl acetate and polyvinylalcohol.

\* \* \* \* \*